US011141556B2

(12) United States Patent
Jantunen

(10) Patent No.: US 11,141,556 B2
(45) Date of Patent: Oct. 12, 2021

(54) APPARATUS AND ASSOCIATED METHODS FOR ADJUSTING A GROUP OF USERS' SLEEP

(71) Applicant: Nokia Technologies Oy, Espoo (FI)

(72) Inventor: Joni Jorma Marius Jantunen, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 194 days.

(21) Appl. No.: 16/253,182

(22) Filed: Jan. 21, 2019

(65) Prior Publication Data
US 2019/0224443 A1  Jul. 25, 2019

(30) Foreign Application Priority Data

Jan. 24, 2018  (EP) .................................... 18153294

(51) Int. Cl.
*A61M 21/02* (2006.01)
*A61B 5/00* (2006.01)
(Continued)

(52) U.S. Cl.
CPC ........... *A61M 21/02* (2013.01); *A61B 5/4812* (2013.01); *G16H 20/70* (2018.01); *G16H 50/20* (2018.01);
(Continued)

(58) Field of Classification Search
CPC ... A61B 5/4812; A61B 5/4815; A61B 5/6815; A61M 21/02; A61M 2205/3303
See application file for complete search history.

(56) References Cited

U.S. PATENT DOCUMENTS 7,041,049 B1 * 5/2006 Raniere ................. A61M 21/02
128/905
9,706,284 B2    7/2017 Lott
(Continued)

FOREIGN PATENT DOCUMENTS

EP       2976993 A2    1/2016
WO    2009/118319 A1   10/2009
WO    2013/009988 A1    1/2013

OTHER PUBLICATIONS

"Sleep Disorder Clinics Industry in the US", IBISworld, Retrieved on Jan. 16, 2019, Webpage available at : https://www.ibisworld.com/industry-trends/specialized-market-research-reports/life-sciences/health-practitioners/sleep-disorder-clinics.html.
(Continued)

*Primary Examiner* — Samuel G Gilbert
(74) *Attorney, Agent, or Firm* — Harrington & Smith

(57) ABSTRACT

An apparatus comprising: at least one processor; and at least one memory including computer program code, the at least one memory and the computer program code configured to, with the at least one processor, cause the apparatus to perform at least the following: receive respective sleep profiles of a plurality of users, each sleep profile comprising recorded sleep phases of a sleep session of a respective user of the plurality of users, receive a target sleep outcome of the plurality of users; and based on the respective sleep profiles and the target sleep outcome, determine one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users.

20 Claims, 7 Drawing Sheets

(51) Int. Cl.
*G16H 20/70* (2018.01)
*G16H 50/20* (2018.01)
*A61M 21/00* (2006.01)
*A61B 5/11* (2006.01)

(52) U.S. Cl.
CPC .......... *A61B 5/1116* (2013.01); *A61B 5/7405* (2013.01); *A61M 2021/0022* (2013.01); *A61M 2021/0027* (2013.01); *A61M 2021/0066* (2013.01); *A61M 2021/0083* (2013.01); *A61M 2205/3553* (2013.01); *A61M 2205/3584* (2013.01); *A61M 2205/50* (2013.01); *A61M 2205/52* (2013.01); *A61M 2230/06* (2013.01); *A61M 2230/42* (2013.01); *A61M 2230/50* (2013.01); *A61M 2230/62* (2013.01); *A61M 2230/63* (2013.01)

(56) References Cited

U.S. PATENT DOCUMENTS

| | | |
|---|---|---|
| 2005/0143617 A1 | 6/2005 | Auphan |
| 2010/0087701 A1* | 4/2010 | Berka ................... A61M 21/02 600/27 |
| 2011/0018720 A1 | 1/2011 | Rai et al. |
| 2011/0021866 A1* | 1/2011 | Iizuka ................... A61B 3/113 600/26 |
| 2011/0230790 A1* | 9/2011 | Kozlov ............... A61B 5/4812 600/595 |
| 2012/0139722 A1* | 6/2012 | Wong ................... A61B 5/1116 340/539.12 |
| 2013/0002435 A1 | 1/2013 | Utter, II |
| 2013/0108995 A1 | 5/2013 | DePasqua et al. |
| 2014/0316192 A1 | 10/2014 | de Zambotti et al. |
| 2015/0092038 A1 | 4/2015 | Jantunen |
| 2015/0092972 A1 | 4/2015 | Lai et al. |
| 2016/0015314 A1 | 1/2016 | Dusanter et al. |
| 2016/0029974 A1 | 2/2016 | Armstrong et al. |
| 2016/0073935 A1* | 3/2016 | van Beest ............. A61B 5/1116 600/529 |
| 2016/0128629 A1 | 5/2016 | Crow et al. |
| 2017/0251295 A1 | 8/2017 | Pergament et al. |
| 2017/0347946 A1 | 12/2017 | Arnold et al. |
| 2018/0125256 A1* | 5/2018 | Tsern ................... G05B 13/024 |

OTHER PUBLICATIONS

"Jabra Elite Sport Earbuds", Jabra GN, Retrieved on Jan. 16, 2019, Webpage available at : http://www.jabra.hk/sports-headphones/jabra-elite-sport.

"The 10 Best Noise Cancelling Earbuds in 2018", Headphones Addict, Retrieved on Jan. 16, 2019, Webpage available at : https://headphonesaddict.com/best-noise-cancelling-earbuds/.

"Headsets Market Size to Reach $20,465.7 Million by 2024", Grand View Research, Retrieved on Jan. 16, 2019, Webpage available at : https://www.grandviewresearch.com/press-release/global-headset-market.

Zhang et al., "Reduction in Time-to-Sleep Through EEG Based Brain State Detection and Audio Stimulation", 37th Annual International Conference of the IEEE Engineering in Medicine and Biology Society (EMBC), Aug. 25-29, 2015, pp. 8050-8053.

Partial European Search Report received for corresponding European Patent Application No. 18153302.7, dated Oct. 12, 2018, 11 pages.

Extended European Search Report received for corresponding European Patent Application No. 18153294.6, dated Oct. 12, 2018, 8 pages.

\* cited by examiner

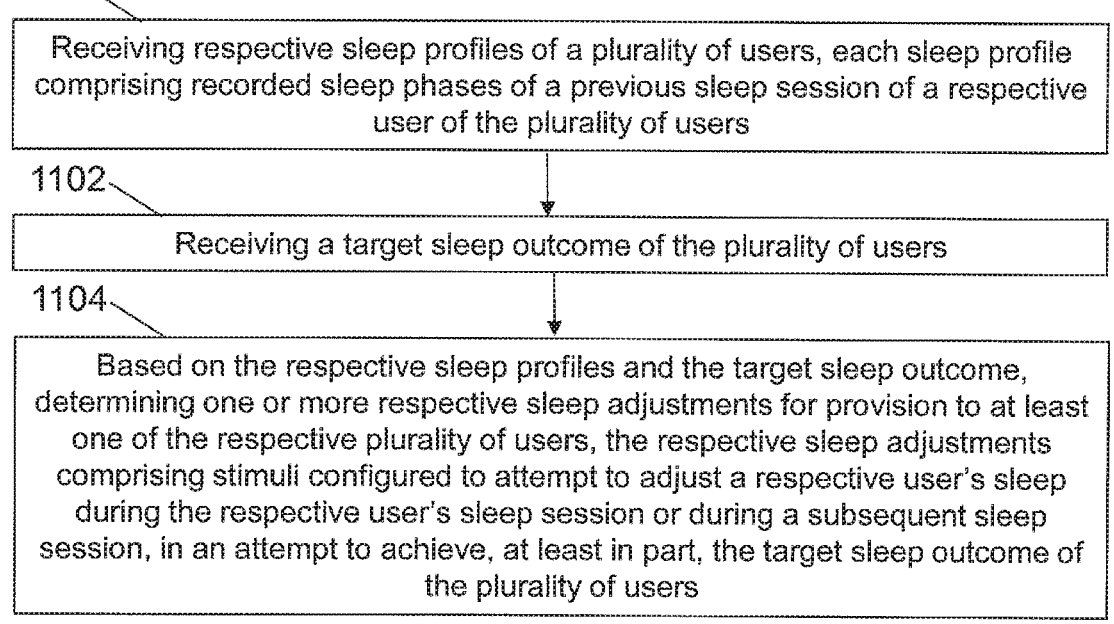
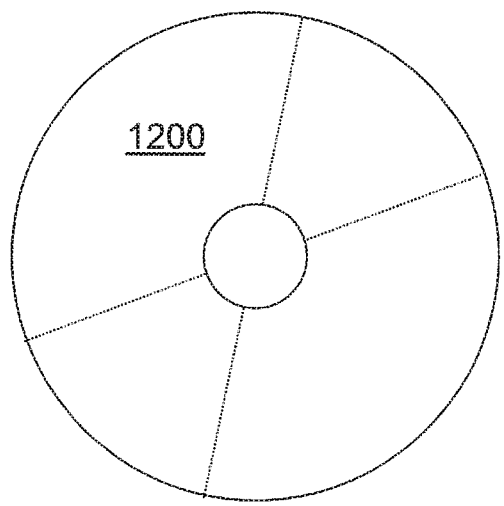

APPARATUS AND ASSOCIATED METHODS FOR ADJUSTING A GROUP OF USERS' SLEEP

TECHNICAL FIELD

The present disclosure relates to apparatus and methods associated with adjusting the sleep habits of one or more of a plurality of users.

Some examples may relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs. Certain portable electronic devices may be wearable, such as on the wrist. The portable electronic devices/apparatus according to one or more disclosed example aspects/embodiments may provide one or more audio/text/video communication functions (e.g. telecommunication, videocommunication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Recent developments in technology include devices used to monitor a user's sleep habits.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising:
at least one processor; and
at least one memory including computer program code,
the at least one memory and the computer program code configured to, with the at least one processor, cause the apparatus to perform at least the following:
receive respective sleep profiles of a plurality of users, each sleep profile comprising recorded sleep phases of a sleep session of a respective user of the plurality of users;
receive a target sleep outcome of the plurality of users; and
based on the respective sleep profiles and the target sleep outcome, determine one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users.

The phrase "during one or more of the respective user's sleep session and a subsequent sleep session" means that the apparatus may be configured to provide the stimuli during one or more of the respective user's current sleep session, and one or more subsequent sleep sessions.

The memory and computer program code may be configured to, with the processor, cause the apparatus to provide the respective sleep adjustments to the plurality of users.

The target sleep outcome may be set for each of the plurality of users such that the plurality of users achieves a common future goal.

The plurality of users may be an established user group, the established user group having a predetermined common future goal.

The memory and computer program code may be configured to, with the processor, cause the apparatus to determine the respective one or more sleep adjustments of the one or more of the plurality of users by using respective sleep biosignals recorded during a sleep session of the plurality of users.

The sleep session during which the sleep biosignals are recorded and/or during which the sleep profiles of the users are determined may be a previous sleep session or the current sleep session.

The target sleep outcome may be one or more of:
determined by the apparatus based on the received respective sleep profiles;
input by one of the plurality of users; and
input by a secondary user other than any of the plurality of users.

The target sleep outcome may comprise one or more of:
two or more of the plurality of users awaking at the same time;
one or more of the plurality of users awaking within a predetermined time window;
two or more of the plurality of users awaking following being asleep for the same amount of time;
two or more of the plurality of users having an asleep-awake daily routine in the same time zone. Connected devices may be controlled by the apparatus during sleep in some examples, e.g. to change the room temperature to a temperature more conducive to remaining asleep.

The target sleep outcome may comprise different individual respective sleep adjustments for provision to each of two or more of the plurality of users.

The target sleep outcome may be an outcome to be achieved following a plurality of sleep sessions. The memory and computer program code may be configured to, with the processor, cause the apparatus to determine respective series of incremental sleep adjustments for provision to the plurality of users over the plurality of sleep sessions to achieve the target sleep outcome.

The sleep biosignal may comprise one or more of:
a position of a user's head;
a position of a user's body;
motion of a user's head;
motion of a user's body;
motion of a user's eyes;
the heart rate of a user;
the breathing rate of a user; and
the temperature of a user
during the sleep session; the user being of the plurality of users.

The memory and computer program code may be configured to, with the processor, cause the apparatus to:
receive respective awake profile data for one or more of the plurality of users, the respective awake profile data comprising a record of activities during a period of being awake for one or more of the respective users; and determine the one or more respective sleep adjustments further based on the awake profile data for the one or more of the respective users.

The respective one or more sleep adjustments may comprise stimuli configured to attempt to adjust the sleep of a respective user of the plurality of users during one or more of the sleep session and the subsequent sleep session by inducing an adjustment in sleeping posture of the user.

The stimuli may be configured to be provided to a user of the plurality of users by one or a pair of earphones to be worn by the user during one or more of the sleep session and the subsequent sleep session.

The apparatus may be a server remote from and in communication with a plurality of output devices, the plurality of output devices configured to provide the stimuli to the plurality of users.

The sleep adjustment may further comprise one or more of: audio stimuli, vibratory stimuli, temperature stimuli, and pressure stimuli. Audio stimuli may comprise one or more of: music, tones, speech, and sounds from nature.

The memory and computer program code may be configured to, with the processor, cause the apparatus to determine one or more awake instructions for provision to one or more users of the plurality of users, the awake instructions indicating an activity for a user of the plurality of users to perform to support the attempt to adjust that user's sleep during one or more of the sleep session and the subsequent sleep session in the attempt to achieve, at least in part, the target sleep outcome.

The apparatus may be configured to determine the identity of a particular user of the plurality of users by determining one or more biosignals indicative of the particular user, and determine a sleep adjustment for the particular user.

The apparatus may be configured to determine whether the duration of provision of the sleep adjustment exceeds a predetermined sleep adjustment threshold, and if it does, prevent the provision of further sleep adjustment until the expiry of a sleep adjustment cooling off period. The predetermined sleep adjustment threshold may be a predetermined number of consecutive sleep sessions (e.g. 7 nights).

In a further aspect there is provided a system comprising:
a control apparatus; and
a plurality of output devices in communication with the control apparatus;
the control apparatus configured to:
  receive respective sleep profiles of a plurality of users, each sleep profile comprising recorded sleep phases of a sleep session of a respective user of the plurality of users;
  receive a target sleep outcome of the plurality of users; and
  based on the respective sleep profiles and the target sleep outcome, determine one or more respective sleep adjustments for provision to at least one of the respective plurality of users, the respective sleep adjustments comprising stimuli configured to attempt to adjust a respective user's sleep during one or more of the respective user's sleep session and a subsequent sleep session in an attempt to achieve, at least in part, the target sleep outcome of the plurality of users; and
  provide the determined one or more respective sleep adjustments to the plurality of output devices;
the plurality of output devices each configured to:
  receive the determined one or more respective sleep adjustments comprising the stimuli from the control apparatus for the user of the plurality of users associated with that output device, and
  provide the stimuli to the associated user during one or more of the respective user's sleep session and the subsequent sleep session.

The sleep biosignals may be captured using one or more of: an accelerometer, a gyroscope, a thermometer, a microphone, a heart rate monitor, a remote monitoring technique, a sleep monitor, a camera, an IR sensor, and RADAR.

The plurality of output devices may be further configured to capture the sleep biosignals.

In a further aspect there is provided a computer-implemented method comprising
  receiving respective sleep profiles of a plurality of users, each sleep profile comprising recorded sleep phases of a sleep session of a respective user of the plurality of users;
  receiving a target sleep outcome of the plurality of users; and
  based on the respective sleep profiles and the target sleep outcome, determining one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users.

The steps of any method disclosed herein do not have to be performed in the exact order disclosed, unless explicitly stated or understood by the skilled person.

Corresponding computer programs for implementing one or more steps of the methods disclosed herein are also within the present disclosure and are encompassed by one or more of the described examples.

In a further aspect there is provided a computer readable medium comprising computer program code stored thereon, the computer readable medium and computer program code being configured to, when run on at least one processor, perform:
  receiving respective sleep profiles of a plurality of users, each sleep profile comprising recorded sleep phases of a sleep session of a respective user of the plurality of users;
  receiving a target sleep outcome of the plurality of users; and
  based on the respective sleep profiles and the target sleep outcome, determining one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users.

One or more of the computer programs may, when run on a computer, cause the computer to configure any apparatus, including a circuit, controller, or device disclosed herein, or perform any method disclosed herein. One or more of the computer programs may be software implementations, and the computer may be considered as any appropriate hardware, including a digital signal processor, a microcontroller, and an implementation in read only memory (ROM), erasable programmable read only memory (EPROM) or electronically erasable programmable read only memory (EE-PROM), as non-limiting examples. The software may be an assembly program.

One or more of the computer programs may be provided on a computer readable medium, which may be a physical computer readable medium such as a disc or a memory device, may be a non-transient medium, or may be embodied as a transient signal. Such a transient signal may be a network download, including an internet download.

In a further aspect there is provided an apparatus comprising means for
receiving respective sleep profiles of a plurality of users, each sleep profile comprising recorded sleep phases of a sleep session of a respective user of the plurality of users;
receiving a target sleep outcome of the plurality of users; and
based on the respective sleep profiles and the target sleep outcome, determining one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users.

The present disclosure includes one or more corresponding aspects, examples or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:
FIG. 11 shows an example method according to the present disclosure;
and
FIG. 12 shows a computer-readable medium comprising a computer program configured to perform, control or enable the method of FIG. 11.

DESCRIPTION OF SPECIFIC EXAMPLES

Recent developments in technology include devices used to monitor a user's sleep habits.

Figure 1:
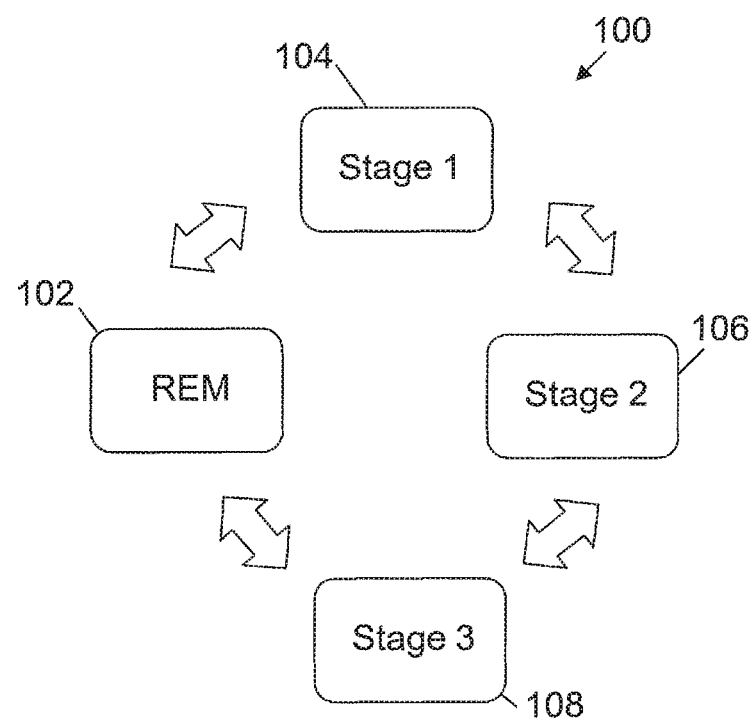
FIG. 1 shows a schematic of a sleep cycle.

FIG. 1 shows a schematic of a sleep cycle 100. From being awake, first a user going to sleep may enter REM (rapid eye movement) sleep 102. REM sleep revitalises the memory. In this stage, brain activity is very high, and intense. Dreaming is likely to occur. REM sleep occurs first in about the first 90 minutes after falling asleep. From REM sleep the user can enter Stage 1 sleep 104. In Stage 1 sleep a user can experience a light transitional sleep. This stage is where drowsiness and sleep begin. In some cases, a user may enter Stage 1 sleep followed by REM sleep. From Stage 1 sleep the user can enter Stage 2 sleep 106. In Stage 2 sleep, more stable sleep occurs.

Chemicals produced in the brain block the senses, making it difficult to be woken. From Stage 2 sleep a user can enter Stage 3 sleep 108, which is deep sleep. Growth hormone is released during this stage. Most Stage 3 sleep occurs in the first third of the night. A user may be woken back through Stages 2, 1 and REM sleep from Stage 3, or may skip one or more stages to be woken. Waking directly from certain stages (such as Stage 2 106 and Stage 3 108 sleep) may leave the user feeling unrefreshed and drowsy. A user being woken from REM 102 or Stage 1 104 sleep may feel more refreshed because they are naturally in a lighter sleep state before being awoken. A user may also feel more refreshed following a sleep session if they have experienced sufficient proportions of the different stages of sleep. Further, experiencing good quality sleep, including sufficient time in certain stages of sleep, may be associated with improved cognitive function and memory following the sleep session. The terms "sleep stage" and "sleep phase" are synonymous.

Examples disclosed herein may aid a user to have improved sleep, and may allow the user to attempt to adjust their sleep habits and patterns in an attempt to achieve, at least in part, a particular target sleep outcome, such as feeling more awake upon waking, achieving a set minimum amount of time of deep sleep, or improving cognitive function, for example.

Figure 2:
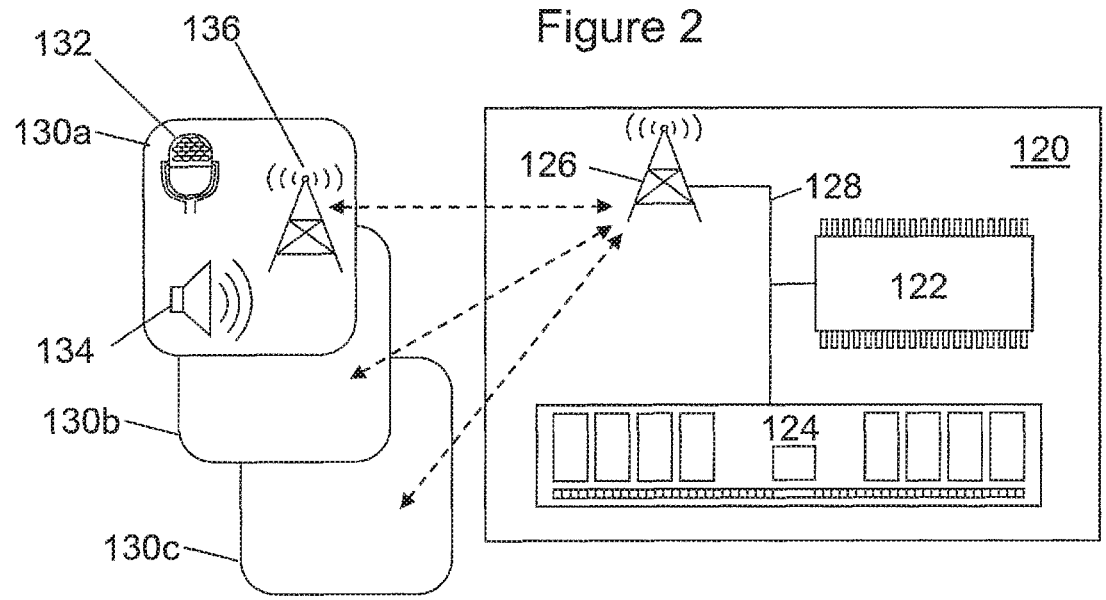
FIG. 2 shows an example apparatus according to the present disclosure.

FIG. 2 shows an apparatus 120 as disclosed herein. The apparatus 120 may, in some examples, be a server remote from and in communication with a plurality of remote output devices 130a, 130b, 130c such as audio devices e.g. earphones or pairs of earphones, and speakers. A speaker may be configured, for example, to sit on a bedside table or under a pillow. In examples where stimuli other than, or as well as, audio stimuli may be provided, the remote output devices 130a, 130b, 130c may comprise one or more of a temperature changing element (e.g. a warmable/coolable element), a pressure changing element (e.g. an inflatable element), and a vibratory element (e.g. a vibrating wearable element). The output devices are configured to provide stimuli to the plurality of users. The apparatus 120 comprises a processor 122 and memory 124 (including computer program code) and a transceiver 126, which are electrically connected to one another by a data bus 128.

Each user of a plurality of users may have their own remote output device 130a, 130b, 130c. The remote output devices 130a, 130b, 130c in some examples may comprise, at least one audio speaker 134 (e.g. as part of an earphone) configured to provide audio output, and at least one microphone 132 configured to receive audio input from the user. In some examples the remote output devices 130a, 130b, 130c may comprise an audio output device 134 without an audio input device 134. The remote output devices 130a, 130b, 130c may also comprise an apparatus (not shown) such as apparatus 120 comprising a memory and processor as described below for apparatus 120, to manage the operation and communication of the remote output devices 130a, 130b, 130c.

The at least one memory 124 and the computer program code are configured to, with the at least one processor 122, cause the apparatus to receive respective sleep profiles of a plurality of users, each sleep profile comprising recorded sleep phases of a sleep session of a respective user of the plurality of users; receive a target sleep outcome of the plurality of users, and based on the respective sleep profiles and the target sleep outcome, determine one or more respective sleep adjustments for provision to at least one of the respective plurality of users. For example, a group of users may be a team of colleagues who are scheduled to fly to Germany for a conference. This plurality of users is an established user group and has a predetermined common future goal of wanting to feel alert and refreshed for the meeting in Germany. The sleeping habits of each user in the group (e.g. the duration and timing of the different phases of sleep) may be recorded (e.g. by remote output devices 130a, 130b, 130c used by the respective users, or by one or more other separate apparatuses). The group of users may have a particular target which they wish to achieve by tuning their sleep habits (e.g. they wish to awake at 6 am feeling refreshed, in time to catch their flight to Germany and with reduces effects of jet lag due to changing time zones). The apparatus can determine a "sleep adjustment" to provide to each user to help achieve the target sleep outcome for the group. Of course, each individual user is likely to have their own individual sleep habits and so the sleep adjustments for each user may be different, but be determined such that the common goal for the group may be attained. Also, if the different users of the group are in different time zones prior to travelling to Germany, they may each require different stimuli to allow for individual time zone adjustments by the provision of different stimuli during sleep.

The respective sleep adjustments in this example comprises stimuli configured to attempt to adjust a respective user's sleep during one or more of the respective user's sleep session and a subsequent sleep session in an attempt to achieve, at least in part, the target sleep outcome of the plurality of users. In some examples, the apparatus 120 may be configured to provide the sleep adjustment for a particular user to the user, for example, as an audio stimulus provided via the speaker(s) 134 of the remote output devices 130a, 130b, 130c of the user.

It is recognised that the stimuli provided to the user may not always cause the users' sleep during a sleep session to be adjusted in the expected manner Therefore, achieving the target sleep outcome may not always be fully realised for one or more of the plurality of users. However, by providing the determined sleep adjustment(s) as described herein, a reasonable attempt is made to adjust the users' sleep during a sleep session in order to help attempt achieve, at least in part, the target sleep outcome. For example, a target sleep outcome of "sleep one hour longer" may not be fully realised for a user, if the user wakes up before the extra one-hour elapses. However, the provided sleep adjustment stimuli may have still helped the user to sleep longer (e.g. 50 minutes), thus achieving, at least in part, the target sleep outcome.

In some examples, the sleep adjustments may be provided to each remote output device 130a, 130b, 130c prior to the sleep session as signals to provide particular stimuli during the upcoming sleep session. The sleep adjustments may be provided with data representing particular signals (such as sounds from nature, spoken word messages, vibration patterns, temperature setpoints or pressure setpoints) as a download for each user prior to the sleep session.

In some examples, the sleep adjustments may be provided to each remote output device 130a, 130b, 130c during the sleep session as real-time or near-real-time signals to provide particular stimuli during the upcoming sleep session. Each user's remote output device 130a, 130b, 130c may already have access to a library of stimuli (for example, audio stimuli stored with the user's remote output device 130a, 130b, 130c or at a remote server/apparatus accessible by the remote output device 130a, 130b, 130c, such as a user computer or smartphone). The sleep adjustments may thus indicate which signal, available in the user's library, should be provided and when it should be provided without requiring files to be downloaded e.g. from the apparatus 120 prior to or during the sleep session.

The processor 122 may be configured for general operation of the apparatus 120 by providing signaling to, and receiving signaling from, the other components to manage their operation. The memory 124 may be configured to store computer code configured to perform, control or enable operation of the apparatus 120. The memory 124 may also be configured to store settings for the other components (for example, communication instructions for the transceiver 126 to communicate with each remote output device 130a, 130b, 130c). The processor 122 may access the memory 124 to retrieve the component settings in order to manage the operation of the other components.

The transceiver 126 may comprise a separate transmitter and receiver and be configured to transmit data to, and receive data from, one or more other devices via a wireless or a wired connection. For example, if the apparatus 120 forms part of a system, the transceiver 126 may be configured to receive information from a remote server or analysis module providing information on stimuli to provide to the user during sleep, and/or transmit information to a remote server or analysis module providing information on audio and/or sensor signals received from the user during sleep, so that the remote server or analysis module may determine the user's sleep phases during a sleep session. The transceiver 126 in FIG. 2 is shown to be in wireless communication with the remote output devices 130a, 130b, 130c each used by a user of the plurality of users.

Figure 3:
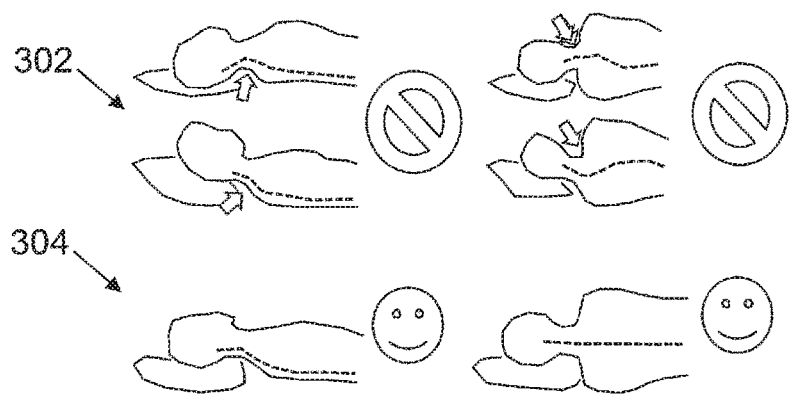
FIG. 3 shows different sleeping postures.

FIG. 3 shows different sleeping postures. Certain postures 302 may be detrimental to achieving a good quality relaxing period of sleep, for example because pressure is placed on the user's neck or shoulders which causes the user to awake feeling tense or unrelaxed. Certain postures 304 may be conducive to achieving a good quality relaxing period of sleep, for example because the user's head, neck and shoulders are positioned and supported in a natural balanced way, allowing the user to sleep and fully relax their upper body muscles, to awake feeling rested and refreshed.

Audio stimuli to be provided to the user to achieve the user's target sleep outcome may cause the user, during sleep, to adjust their body posture and rest in a more relaxing posture 304 to help achieve improved quality sleep. For example, providing an unpleasant audio stimulus in the user's right ear may cause the user to roll over from their right side (in an uncomfortable posture 302) to their back (in a comfortable posture 304), allowing the user to more easily enter a deeper sleep, at which point the audio stimulus may cease, allowing the user to sleep in a quiet environment. Apparatus disclosed herein such as the apparatus 120 described in relation to FIG. 2 may determine (and, in some examples, provide) a sleep adjustment for a user comprising stimuli, such as audio stimuli, which is configured to attempt to adjust the user's sleep during the sleep session by inducing an adjustment in sleeping posture of the user. The sleep session may be a current sleep session, e.g. in which the user's poor sleep posture is detected and attempted to be improved just after the time of detection in the same sleep session, through the provision of stimuli. The sleep session may be a subsequent sleep session, for example, following detection for three nights of the user snoring, it may be determined that the snoring is a persistent habit and in the next sleep session, the apparatus attempts to reduce the snoring, for example, by inducing a change in sleeping posture of the user through the provision of stimuli. Such apparatus may be in communication with one or more sensors located with the user (e.g. a part of the remote output device 130a, 130b, 130c) which are configured to detect the current posture of the user and provide this information as feedback to the apparatus 120, so the apparatus 120 is provided with the user's posture as input. Thus, the apparatus 120 receives e.g. input indicating the position of the user, so if the provided stimuli is intended to induce a posture change, the apparatus can be informed of how and when the posture change has taken place.

For example, a plurality of users may be a hockey team who have to meet at 8 am at the sports ground to prepare for a match. This plurality of users is an established user group and has a predetermined common future goal of performing well at the next-day hockey match. As an example, the apparatus may check and adjust, by the provision of stimuli to the team members requiring it, one or more team member's sleeping posture to a better posture so that everyone in the team achieves a well-rested night's sleep to help their collective sporting performance the next day.

The target sleep outcome may comprise different individual respective sleep adjustments for provision to each of two or more of the plurality of users. For example, the apparatus may take account of the different sleep habits of the individual users. If one user usually requires seven hours of sleep per night, and another user usually required nine hours of sleep per night, this may be factored in to the provision of stimuli to those users in attempting to achieve the target sleep outcome. For example, if the two users are partners who share night-time waking duties (to attend to a child, for example), the apparatus may consider the individual users' usual sleep habits when providing stimuli to e.g. wake one partner up while keeping the other partner asleep. The partner who usually sleeps for less time overall may be woken more than the partner who requires more sleep.

It is to be appreciated that the apparatus 120 may determine that one or more users do not require the provision of stimuli, and so the stimuli is not provided to those users (e.g. because the apparatus determines that the one or more users already have a posture conducive to achieving a good quality relaxing period of sleep). Therefore, a target outcome may be configured for a plurality of users, but the provision of a sleep adjustment comprising stimuli may be provided to one, some or all of the plurality of users, as appropriate. In some examples, a sleep adjustment of "no change" may be determined for one or more of the plurality of users. That is, one or more of the plurality of users may receive no stimuli as the apparatus has determined it not to be necessary to achieve the target sleep outcome.

Figure 4:
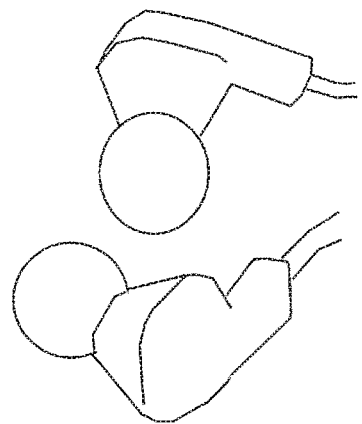
FIG. 4 shows an example audio output device according to the present disclosure.

FIG. 4 shows an example audio output device according to the present disclosure, such as a remote output device 130a, 130b, 130c in FIG. 2. In some examples, audio stimuli may be provided to each user of the plurality of users by one or a pair of earphones to be worn by the user during a sleep session. In other examples, audio stimuli may be provided by a standalone (non-earphone) speaker or group of speakers to each user. A user who shares a room or bed with another person may prefer using in-ear earphones to avoid disturbing the sleep of the other person. A person who sleeps alone may prefer receiving audio stimuli via a non-earphone based speaker, so they do not have to wear any apparatus while sleeping. Earphones may be wired, half-wired (in which the two earphones are connected to each other by a wire but may be in wireless communication with a control unit), or may be wireless (wireless or half-wired earphones may be preferred to allow for movement during sleep without the possibility of pulling/tangling the earphone wires). Wireless earphones may require two separate transceivers, one for the left earphone and another for the right earphone. In-ear earphones such as those shown in FIG. 4 may be "noise cancelling" and thus configured to decrease the volume of ambient noise detected by the user's ears. In some examples, the audio stimuli may be provided by way of active noise cancellation, in an attempt to attenuate any background noise and allow the user to sleep in a quieter environment.

Figure 5:
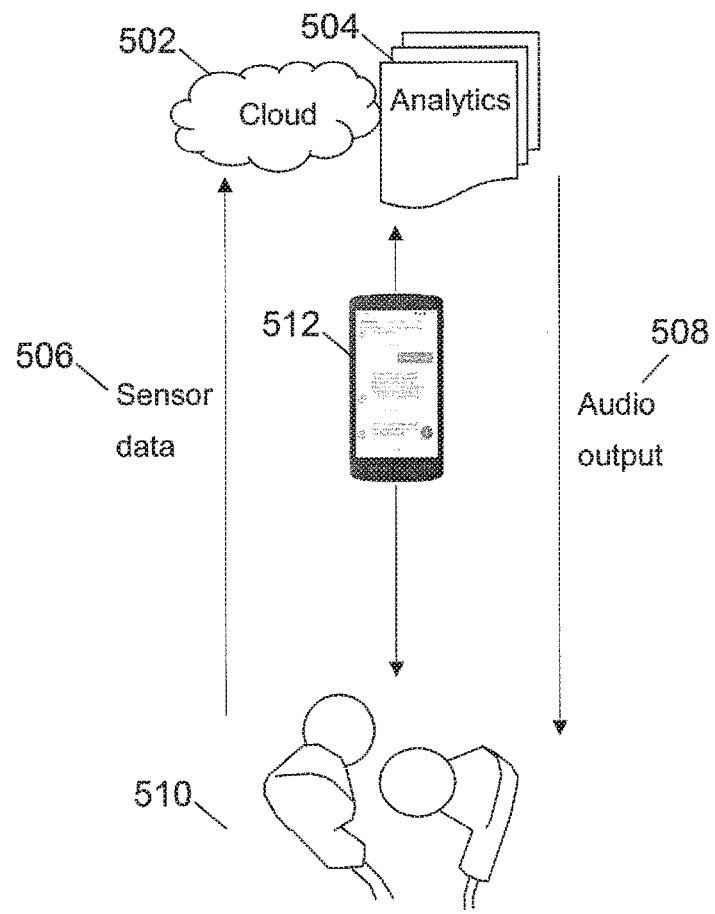
FIG. 5 shows an example system according to the present disclosure.

FIG. 5 shows an example system according to the present disclosure. This example shows a system comprising an audio/sensor device (earphones) 510 configured to provide a user of a plurality of users with audio stimuli during sleep. An analysis module 502, 504, which may be a remote server 504, or may be the "Cloud" 502, is in communication 508 with the audio output device 510, and is configured to indicate or provide audio stimuli to provide to the user. Also in this example, sensor data 506 (e.g. audio data detected using a microphone, gyroscope data indicating a sleeping posture) from the sleeping user is provided from the audio/sensor device 510 to the analysis module 502, 504.

FIG. 5 also indicates an intermediary apparatus 512, which may, for example, be a user device such as a smartphone or tablet computer. This intermediary device 512 may be configured to receive data (e.g. posture and sleep phase data) from the audio/sensor device 510 for analysis and/or provision to the analysis module 502, 504, and/or configured to receive data (e.g. an indication of audio stimuli to provide to the user) from the analysis module 502, 504 for provision to the audio/sensor device 510.

In such a system, each user of the plurality of users may have their own audio output device 510, and if using an intermediate device 512, each user may have their own intermediate device 512. The analysis module 502, 504 may be common to all the users of the plurality, and may therefore receive sensor data from the plurality of users, and provide audio output individually to the plurality of users in the group. FIG. 5 thus illustrates the system in respect of one of the plurality of users.

In some examples, the target sleep outcome of the plurality of users may be determined by the apparatus based on the received respective sleep profiles. For example, each audio/sensor device 510 may detect the users' phases of sleep during one or more (e.g. previous) sleep sessions, and from these determine the sleep patterns of the users. The apparatus may be configured to determine the respective one or more sleep profiles for one or more of the plurality of users by using respective sleep biosignals recorded during a (previous and/or current) sleep session of the plurality of users. A sleep biosignal may comprise one or more of: a position of the user's head; a position of the user's body; motion of the user's head; motion of the user's body; motion of the user's eyes; the heart rate of the user; R-R intervals of the user's heartbeat and variations thereof; the breathing rate of the user; the skin conductivity of the user, and the temperature of the user during the sleep session, the user being of the plurality of users.

For example, a user's sleep profile may show that they regularly take a long time (e.g. longer than the average time for a user of a matching demographic) to achieve Stage 2 or Stage 3 sleep (a deep sleep). The time taken to fall asleep may be detected, for example, by one or more sensors (for example by a microphone) measuring background noise levels. Background noise may decrease, or may change character, from when the user is awake (e.g. breathing more quickly and/or loudly, and moving around in bed) and asleep (quieter and/or slower breathing, and less body movement). The target sleep outcome for a plurality of users, of which this user is a member, may be to attend a meeting at 10 am the next day. Thus, the user's individual target sleep outcome may be to achieve Stage 2 or Stage 3 sleep in a shorter time following the start of a sleep session, as this may help the user achieve a more refreshing overall sleep session and be awake and alert at the meeting at 10 am the following morning.

As another example, a plurality of users may be a mother and father with two young children. The target sleep outcome of the plurality of users may be that both users (mum and dad) want to feel refreshed at 7 am when the children need to be washed, dressed, and eat breakfast before being taken to nursery at 8 am. The mother is determined to often wake, or be in a very light sleep (REM or Stage 1 sleep) between 3 am and 7 am, as shown in her determined sleep profile. Maintaining a deeper sleep between the hours of 3 am and 7 am may attempt to be achieved by providing her with stimuli conducive to her being in a deeper sleeping state during 3 am and 7 am. The apparatus may determine this sleep adjustment for provision to her. This deeper sleep may help her feel refreshed in the morning when the children need her attention.

The father regularly goes to bed late, after 12 midnight, as shown in his determined sleep profile, and finds it difficult to wake up at 7 am to help with the children. He may benefit in the morning from having had a longer overall period of sleep. Thus, he may receive "awake instructions" telling him to go to bed before 11 pm in order to have an overall longer time asleep before waking at 7 am. His awake instructions may be simply an alarm set on his smartphone telling him to go to bed at 11 pm. He may also receive further awake instructions to help him get to sleep at this earlier time, for example by not using a screen-based gadget after 10 pm, by not eating a heavy meal after 8 pm, or by having a warm bath before going to bed at 11 pm, for example. This is an example of the apparatus being configured to determine one or more awake instructions for provision to one or more users of the plurality of users. The awake instructions indicate an activity for a user of the plurality of users to perform to attempt to support the adjustment of that user's sleep during the subsequent sleep session in an attempt to achieve, at least in part, the target sleep outcome.

As another example, a user of a plurality of users may be detected to stay in REM or Stage 1 sleep for a significant (e.g. more than 50%) of the time during the night. The user has a wake-up alarm set for 6 am so that he can meet a group of friends at 7 am to travel on holiday together. The user's sleep profile may indicate that the user struggles to wake up and get out of bed when required, especially at an early wake up time (e.g. before 10 am). The target sleep outcome of the plurality of users may be that everyone is assembled at the train station to catch a train at 7 am. The user therefore needs to be fully awake and out of bed at 6 am to get ready and meet his friends. This goal may be achieved by the apparatus determining, and in some examples providing, for example, stimuli to wake the user up more fully at 6 am, providing stimuli during sleep to attempt to induce a deeper sleep when the user is in a prolonged REM or Stage 1 sleep stage/phase, and/or by suggesting the user goes to bed earlier than normal and providing stimuli to attempt to induce sleep at the earlier time.

As a further example, a user may be determined to snore during Stage 1 sleep and then move to lighter REM sleep, wherein the user may benefit from stopping snoring to help them move from Stage 1 to a deeper Stage 2 sleep. The user's sleep profile may be determined using a microphone to pick up the snoring sounds, for example. This user is a teacher and often feels tired in the afternoon at work. A common goal for a plurality of users (e.g. the teachers at the user's school), including this user, may be to feel more awake during the working day (e.g. from 8.30 am to 3.30 pm). The apparatus may determine (and may provide to the user) stimuli to counteract the adverse health condition of snoring, and induce the user to e.g. change posture to stop snoring, and move into a deeper sleep. This may help him to feel more awake during the working day. Other possible health-related adverse sleep conditions include sleep apnoea, insomnia, sleep deprivation, nightmares, night terrors, and restless legs syndrome (Willis-Ekbom disease), and one or more of these conditions may be detected by one or more sensors, and used to determine the user's sleep profile and a possible sleep adjustment for that user to counteract the adverse effects of the detected condition.

In some examples, the apparatus may mine data from one or more other user applications to suggest and/or set a target sleep outcome for the plurality of user. For example, the apparatus may have access to users' calendars, and current locations, and determine if the plurality of users have a common upcoming early morning or late night meeting, or are scheduled to all be in a common time zone (e.g. for a business meeting). The apparatus may then suggest a target sleep outcome to help the users each feel better for the scheduled event and may determine respective sleep adjustments for the plurality of users to help them achieve the common future goal of being awake and refreshed for the meeting. If one user of the plurality does not need to change time zones, and is usually a good sleeper, they may not require any sleep adjustments to be provided to achieve the common future goal. Another user of the plurality may need to fly to the meeting destination, and therefore change time zones, and may also be a poor sleeper. This user may be provided with stimuli for one or more sleep sessions prior to the scheduled meeting to adjust that user's sleep to help achieve the target sleep outcome of being alert and refreshed for the meeting.

As another example, a plurality of users may be a revision group studying for an examination. The group members may wish to try and learn during their sleep, and so their target sleep outcome may be to improve their knowledge or ability in a particular subject e.g. speaking a foreign language or another subject such as history. Such users may, for example, then receive audio stimuli comprising learning/revision material (e.g. foreign language tuition/conversation, a spoken recitation of historical events) during the phases of sleep most conducive to the user retaining the audio information received during sleep. Each user in the group may receive similar learning material during the same night's sleep, for example so they can discuss it together the next day.

In some examples, the target sleep outcome may be an outcome to be achieved by one or more of the plurality of users following a plurality of sleep sessions. The apparatus may be configured to determine respective series of incremental sleep adjustments for provision to one or more of the plurality of users over a plurality of sleep sessions to achieve the target sleep outcome. For example, if the target sleep outcome is for a group of colleagues based in different worldwide cites to be prepared/awake for a video conference, one of those colleagues may me attending the video conference at 4 am local time when they would usually be asleep. To adjust that user to the time zone of the video conference, which is e.g. eight hours behind the user's current time zone, then a plurality of incremental sleep adjustments may be made over a period of four nights/sleep sessions prior to the meeting so that the user is gradually adjusted to the time at which the meeting will take place and may attend the meeting in an awake and refreshed state.

In some examples, the target sleep outcome may be determined by input by one of the plurality of users. For example, the plurality of users may be a family with teenage children. The father may provide input instructing the apparatus to determine stimuli to help the teenagers fall asleep quicker (e.g. if they sometimes struggles to get to sleep), to wake up at a certain time pre-set by the user (e.g. to ensure they are awake to go to college), prolong one or more sleep phases (e.g. to try and improve an awake-time feeling of being well rested), or, for example, determine stimuli to cause the users generally to feel more refreshed, improve their memory, have a deeper sleep, or sleep in more comfortable positions. The target sleep outcome for the family may be that everyone is awake enough to get to their respective morning appointments (e.g. college and work feeling well-rested.

In some examples, the target sleep outcome may be determined by input by a secondary user other than the user. For example, a doctor may wish to help improve the sleep of a group of patients on a hospital ward, a relative or carer may wish to improve the sleep of an elderly couple who they care for, or a sports coach/manager may wish to help the members of a sports team achieve a particular sleep goal (e.g. be awake and refreshed for a match/competition the next day).

Some user-set and secondary user-set target sleep outcomes may be pre-set in the apparatus/device (e.g. "I want the group to feel more refreshed", "I want the group to be more alert when they wake up", "I want everyone in our team to be adjusted for a change to the GMT time zone in Y days' time"). Other user-set and secondary user-set target sleep outcomes may be freely entered (not pre-set), such as "please wake us up at X o'clock tomorrow", "We are flying to China in three days' time, please attempt to adjust our sleep patterns so we don't feel so jet-lagged", or "my husband is tired, please help me get to sleep early tonight so we are both refreshed for the weekend".

As mentioned above, there are many different scenarios in which a plurality of users may benefit from one or more of the plurality of users receiving stimuli to attempt to achieve a particular target sleep outcome for the plurality. In general, the target sleep outcome may comprise one or more of the plurality of users: awaking at the same time (e.g. to attend a meeting), awaking within a predetermined time window (e.g. for a user in a family to adjust his/her body-clock following finishing a series of night-shifts at work), awaking following being asleep for the same amount of time (e.g. a couple sharing the amount of awake and asleep time each gets following their new baby being more), and having an asleep-awake daily routing in the same time zone as each other (e.g. if one or more users is changing time zone for a meeting).

In some examples, the apparatus may receive respective awake profile data for one or more of the plurality of users, the respective awake profile data comprising a record of activities during a period of being awake for one or more of the respective users; and determine the one or more respective sleep adjustments further based on the awake profile data for the one or more of the respective users. For example, if a user regularly eats a large evening meal late at night (e.g. 10 pm) the apparatus may determine that the user would benefit from going to bed at least an hour after eating, e.g. at 11.30 pm, so that the user, along with others in the plurality, feel well rested following a sleep session (e.g. the user's may be colleagues, family members, or members of a sports/games team). As another example, if a user is part of a sports team and the team takes part in a sports match during the daytime, the users may all benefit from going to bed an hour earlier than usual the night after the match, and sleeping for an hour longer than usual, to help recover from the physical exertion of the sports match in which they all participated.

In some examples, additionally or alternatively to the audio stimuli provided to help achieve a target sleep outcome, the apparatus may determine that the sleep adjustment comprises one or more of: vibratory stimuli, temperature stimuli, and pressure stimuli. Such stimuli are configured to attempt to adjust the sleep of a user of the plurality of users during the sleep session in an attempt to achieve, at least in part, the target sleep outcome. For example, a user may use a pillow which can be controlled to change temperature, and the apparatus may provide a signal to the pillow to change temperature to help the user achieve a target sleep outcome (e.g. cool the pillow down on a hot night to help the user achieve the target sleep outcome of feeling awake in the morning, by getting into a deeper sleep more quickly).

As another example, the apparatus may provide a signal to a mattress which can vibrate in particular regions to help a user change posture and achieve a target sleep outcome. For example, the user may be in a couple, and the target sleep outcome is that the user snores less so that both partners get a better quality night's sleep. The snoring user may be induced, by audio stimuli provided to the user's right ear and vibrations from the mattress under the right side of the user's body, to roll over onto the left side of the body to stop the snoring. Then, both partners can sleep better. As another example, an in-ear earphone may be configured to inflate and deflate, and the pressure changes provided to the user's ear by the in-ear earphone may be used alongside audio stimuli to help the user e.g. change posture, or help block out detected ambient noise.

As another example, a pillow configured to change shape, such as a pillow comprising a matrix of inflatable/deflatable cells, may be used to control the pressure experienced at different regions of the user's head and neck during sleep (e.g. in a similar way to a pressure controllable mattress used to treat patients suffering from bedsores). The pressure changes provided to the user's head and neck by the pillow may help the user change posture to attempt to achieve a target sleep outcome of two partners sharing a bed getting a more restful night's sleep. The pillow shape may be controlled based on one or more of the current detected posture and pressure of the user during sleep, and/or previous head and neck postures determined and recorded in the user's sleep profile.

In some examples, the apparatus may be in communication with a home automation system (or an "Internet of Things" system) in which household appliances and devices can communicate with each other. The apparatus may, for example, provide audio stimuli to help a user wake up, and in combination with these stimuli, the apparatus may send a signal to a connected air conditioning system, or heating system (for example) to change the air temperature of the room so that it is at an appropriate temperature for the user to wake up in a pleasant environmental temperature. As another example, the apparatus may provide a signal to a connected radio or music player so that the user wakes up to playing music, to help the user wake up fully and not drift back off to sleep. Connected devices may be controlled by the apparatus during sleep in some examples, e.g. to change the room temperature to a temperature more conducive to remaining asleep.

Figure 6:
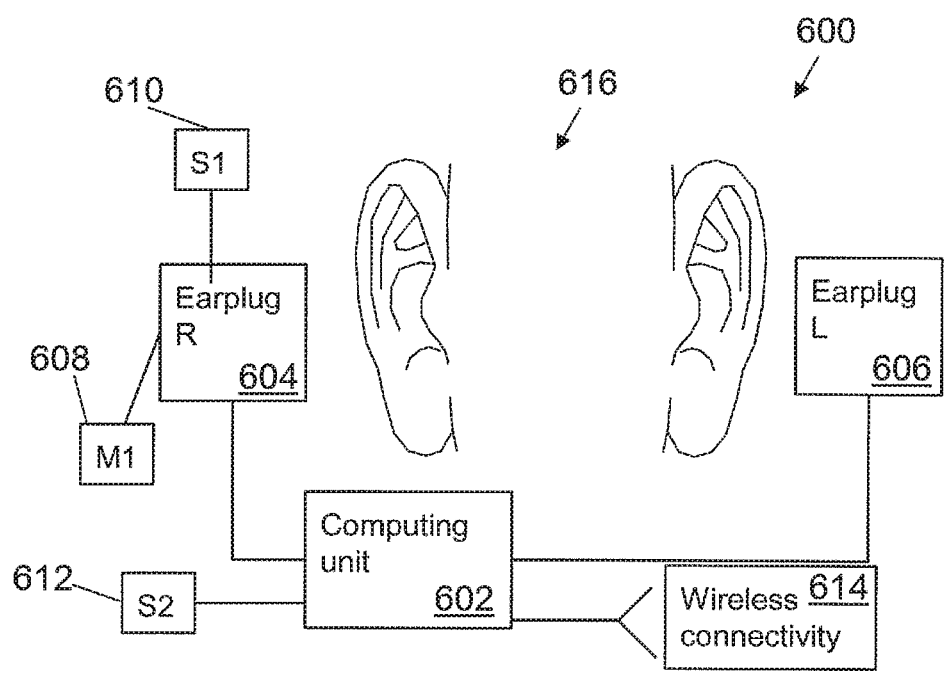
FIG. 6 shows an example apparatus according to the present disclosure.

FIG. 6 shows an example apparatus 600 according to the present disclosure which may be the remote output devices 130a, 130b, 130c of FIG. 2. The apparatus 600 comprises a computing unit 602 which may be similar to the apparatus 120 described in relation to FIG. 2 (e.g. may comprise a memory and processor). The apparatus 600 comprises a right earphone 604 and a left earphone 606 to be worn by the user 616 and which are configured to output audio stimuli. In other examples there may be only one earphone 604, 606 in use. The apparatus 600 also comprises a transceiver 614 for wireless connectivity, e.g. to an external analysis unit, remote peripheral computing apparatus, or the internet. The right earphone 604 is connected to a microphone sensor M1 608 which can detect the user's breathing/snoring/talking during sleep, for example, and to a sensor S1 610 which may, for example, be a temperature, motion, or posture sensor. The computing unit 602 in this example also is connected to a sensor S2 612, such as an ambient noise microphone or ambient temperature sensor. The earphones 604, 606 may generate high quality audio sounds as audio stimuli selectively to both ears (e.g. in mono, stereo, or in 3D audio). The computing unit 602 may be connected wirelessly to an application (e g running on a user peripheral device such as a tablet computer), and/or to the internet/ Cloud. The apparatus 600 may manage data transfer (e.g. of audio output from a remote server to the earphones 604, 606), data analysis (e.g. logging a user's sleep habits), generation of audio stimuli for the user, and the selection of physical and other reactions to the provided stimuli (e.g. determining the effect of the provided audio stimuli for inclusion in a feedback process to guide the stimuli to be provided in future).

The apparatus 600 is described herein as earphone(s) which may be configured to fit in the user's ear canal. However, it should be appreciated that alternative types of ear-worn apparatus 600 may be used. The alternative ear-worn apparatus 600 may be configured with the same features as described above for the earphone example. Examples of alternative ear-worn apparatus include: headphones configured to be worn on or over the user's ears; and one or a pair of in-ear earbuds configured to be worn in the user's ear but that rest outside of the user's ear canal. For convenience, we refer to the ear-worn examples of the apparatus as earphone(s) from hereon.

Figure 7:
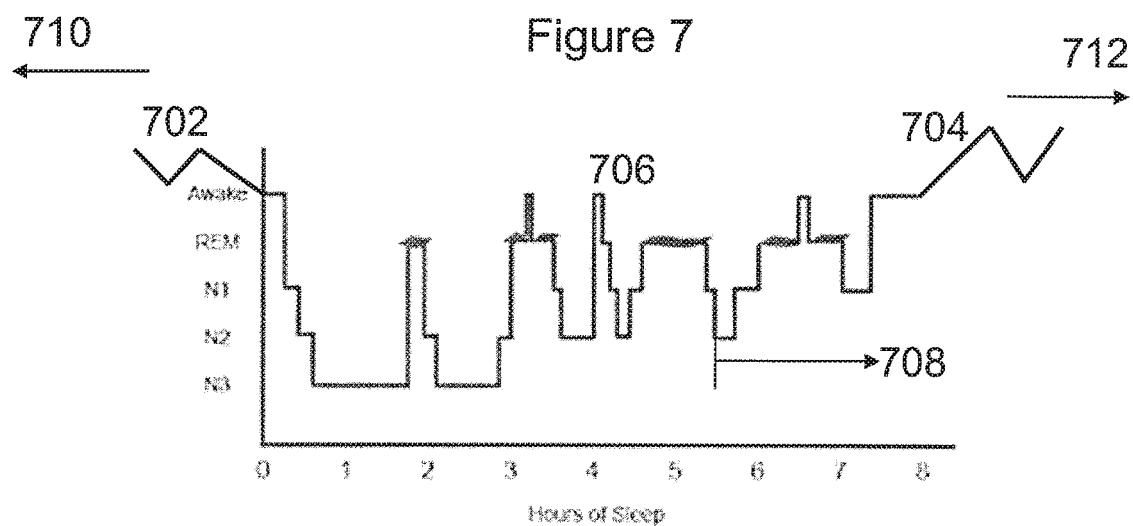
FIG. 7 shows an example of sleep phases experienced by a user during a sleep session.

FIG. 7 shows an example of sleep phases experienced by a user during a sleep session. Hours of sleep are plotted on the x-axis against the phase of sleep experienced (as described in relation to FIG. 1). The user in this example undergoes eight hours of sleep. Different examples of individual target sleep outcomes are indicated in FIG. 7, which may be induced in a user of a plurality of users to achieve a common goal for the plurality.

Prior to going to sleep 702, a user may be instructed to perform certain tasks, at certain times, to facilitate the process of getting to sleep in a way suitable for the user (e.g. taking into consideration the user's usual daily schedule). For example, a user may wish to have eight hours sleep and be awake at 6 am for a morning run with friends. Thus, the user may be instructed to be in bed at 9.30 pm and, for half an hour, read a book or listen to some gentle music to help the user relax. The user may then be instructed to turn off the lights at 10 pm. Other users in the running group may also receive particular audio stimuli to help them each individually achieve a good night's sleep and be awake ready to run at 6 am.

Following the sleep session, a user of a plurality may be awoken 704 in a way which meets the target sleep outcome for the plurality of users. For example, if the user wishes to awake feeling refreshed and be awake for 7 am, the apparatus may provide audio stimuli to make the user up at, or just before 7 am (e.g. an alarm sound gradually increasing in volume). The apparatus may, from previous sleep sessions, and/or from measuring biosignals during the current sleep session, determine that the user is undergoing REM sleep between 5.40 am and 6 am, and that this is a good phase of sleep to be awoken from to feel refreshed, and that the user may be awoken from these lighter sleep phases by a gentle, calm alarm sound such as birdsong. The apparatus may also similarly determine that between 6.15 am and 6.45 am, the user is undergoing Stage 2 or Stage 3 sleep, and that the user should not be awoken during these sleep phases because the user will likely wake up feeling unrefreshed/stressed because they were in a deep sleep, and/or may require a loud unpleasant alarm (e.g. an alarm bell or buzzer) to be awoken from these phases of sleep anyway.

During the night's sleep 706, the apparatus may provide audio stimuli to mitigate the risk of a user waking up if they are not required to. For example, the apparatus may detect (e.g. using a microphone), or receive a signal from an external apparatus indicating the detection of ambient noise (e.g. a neighbour's car alarm sounding, a group of people passing the house chatting noisily). The apparatus may determine (and in some examples, provide, e.g. via earphones) a counter-audio signal to help the user maintain their sleep. Such a signal may, for example, by a relaxing tone, nature sounds, or a background "white noise" to try and counter-balance the potential waking effect of the ambient noise.

The apparatus may be configured to determine the nature of an ambient noise and, based on the determined nature, provide audio stimuli to counter-balance the ambient noise to maintain the user's sleep state (as discussed above) or provide audio stimuli to cause the user to wake gently if it is determined that the user should wake up as a result of the ambient noise. For example, a detected noise may be of a baby crying in the next bedroom to her parents. The target sleep outcome for a family may be that everyone wakes up feeling as refreshed as possible. Thus, in this example, the sleep profiles of one or more previous night's sleep, and/or the biosignals recorded for the current night's sleep, of each parent may be analysed. The parent who has had the better-quality sleep may be selected as the parent to be woken up by audio stimuli designed to wake the user up and attend to the baby crying (e.g. an alarm bell). The parent with the less high-quality sleep may be selected to remain asleep, and may receive audio stimuli designed to maintain a sleep state (e.g. relaxing sounds). In this way, the baby is attended to, and each parent has a reasonable night's sleep, with the "waking duties" of attending to the baby being shared out. Thus, the apparatus may aim to allow certain users to sleep through noises which do not require their attention, but other users to be awoken for noises which do require their attention.

The apparatus may, in some examples, provide audio stimuli to try and prolong 708 one or more phases of the user's sleep. FIG. 7 shows the apparatus has identified that it may benefit a user if their N2/Stage 2 sleep phase following 5.5 hours of sleep is prolonged. The apparatus may, for example, provide relaxing audio stimuli during this sleep phase to try and prolong it. For example, it may be that a target sleep outcome is to have improved focus in the mornings, and that prolonging a particular sleep phase has been indicated to help a particular user achieve that goal.

Preparation for a sleep session aiming for a target sleep outcome may begin prior to the user going to sleep 710. As discussed earlier, the user may be provided with instructions for activities to undertake just before going to sleep 702. In some examples the user may also receive instructions and guidance for activities to do and not do during the daytime several hours before the user is due to go to sleep. In some examples, daytime activity of the user may be provided as input to the apparatus and processed as part of the determination of audio stimuli to provide to attempt to achieve a target sleep outcome. For example, if a user has a stressful commute home between 5 pm and 6 pm, this high stress activity may be accounted for by the apparatus (which may determine particular audio stimuli (e.g. an extended "wind down" period of REM sleep and/or Stage 1 sleep) to help counteract the effect of the stressful commute home.

Similarly, a user may be provided with instructions following sleep 712 to aid the user with their target sleep outcome. For example, users in an exam revision group, aiming to achieve the target sleep outcome of improved focus for an upcoming exam, may be instructed not to use an electronic device for the first hour following waking to help them wake gently. Also, in some examples, a target sleep outcome for the following night's sleep session 712 may be accounted for so that the audio stimuli may be provided before the following sleep session 712, for example during the day, in an attempt to help to achieve the target sleep outcome.

Sleep biosignals of a user may be captured using one or more of: a device located with the user, a microphone (to detect the user's breathing and/or snoring, and/or to detect ambient sounds), an accelerometer, a gyroscope, a posture detector, a motion detector, a thermometer (to measure the temperature of the user's body, the user's skin, and/or the ambient temperature), a heart rate monitor (optical and/or electrical), an electroencephalogram (ECG) detector, a photoplethysmogram (PPG) detector, a ballistocardiograph (BCG) detector, a skin conductivity detector, a skin moisture detector, a body impedance detector, a device located remote from the user, a sleep monitor, a camera, an IR sensor, and radar.

In some examples, the apparatus may be configured to determine the identity of the particular user by using one or more detected biosignals indicative of the particular user, and determine a sleep adjustment for the particular user. The apparatus may be configured to determine the identity of the current user, for example by the user entering a user identifier (e.g. password, passcode, fingerprint, voiceprint) and/or by the apparatus determining the identity of the user without conscious identification input from the user (e.g. by receiving an indication of determined skin conductivity, ear shape, fingerprint, or other bioindicator characteristic of a particular user). The identified user's profile may then be accessed (e.g. personal previous sleep profiles and/or target sleep outcomes) for determination of audio stimuli for a sleep session for that particular user. In some examples, determination of the identity of the user may be used as confirmation that the particular user has rights/permission to use the apparatus (e.g. the user has a licence/software permission).

Figure 8:
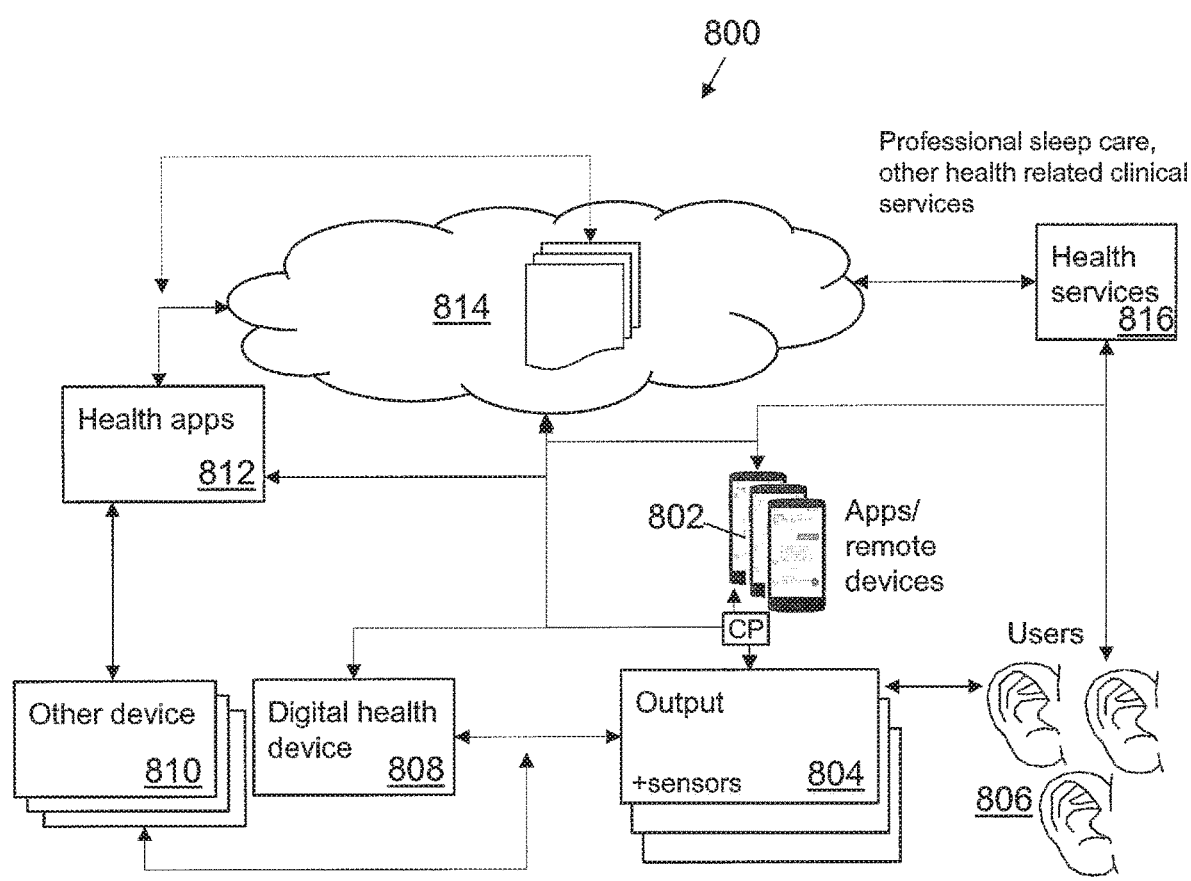
FIG. 8 shows an example system according to the present disclosure.

FIG. 8 shows an example system 800 according to the present disclosure. The system comprises at least a control apparatus 814, and one or a pair of earphones 804 in communication with the control apparatus 814 via a plurality of remote user devices 802 such as smartphones. The control apparatus 814 is configured to: receive respective sleep profiles of a plurality of users 806, each sleep profile comprising recorded sleep phases of a sleep session of a respective user of the plurality of users 806; receive a target sleep outcome for the plurality of users 806, and based on the respective sleep profiles and the target sleep outcome, determine one or more respective sleep adjustments for provision to at least one of the respective plurality of users 806. The respective sleep adjustments comprise audio stimuli configured to attempt to adjust a respective user's sleep during one or more of the respective user's sleep session and a subsequent sleep session in an attempt to achieve, at least in part, the target sleep outcome of the plurality of users 806. The control apparatus 814 is also configured to provide the determined respective sleep adjustments to the plurality of audio output devices 804. This may be provided via an intermediate apparatus 802 such as a user smartphone, and/or directly from the control apparatus 814 to the audio output devices 804. The plurality of audio output devices 804 are each configured to receive the determined respective sleep adjustments comprising the audio stimuli from the control apparatus 814 for the user of the plurality of users 806 associated with that audio output device 804, and provide the audio stimuli to the associated user 806 during the sleep session.

The audio output devices 804 may also comprise one or more sensors to determine signals from the respective associated users for use in determining a user's sleep habits as discussed above.

FIG. 8 also shows at least one digital health device 808 in communication with the control apparatus 814 and the audio output device 804. A further device 810 is also shown in communication with the digital health device 808 and the audio output device 804. The digital health device(s) 808, and the further health device 810 may provide one or more additional stimuli to respective users to aid their sleep, such as lighting. The one or more other devices 801 may in some examples comprise one or more sensors configured to determine/monitor an associated user's sleep state, such as a motion sensor or ambient temperature monitor.

One or more health applications 812 may be in communication with the digital health device 808, the one or more other devices 810, with the audio output devices 804, and with the control apparatus 814. Health services 816 (e.g. hospitals, doctors, clinics, therapists) may be in communication with the control apparatus 814, with the user peripheral devices 802, and with the user 806, to determine a user's sleep habits/issues and provide advice to the users 806. Such services 816 may be professional sleep care services, and other health care related services. Thus, data regarding the user such as the user's sleep profile, target sleep outcome, and/or one or more detected biosignals from the user may be provided securely to the health services 816 to aid in the provision of healthcare and lifestyle management of the user.

The control apparatus 814 may determine the user's sleep phases for the respective users in the plurality of users, during respective sleep sessions, from data recorded by one or more sensors e.g. with the audio output device 804 or other devices 810, and/or may determine and/or provide audio stimuli (and any other additional stimuli) to provide to the users during a sleep session to attempt to achieve the target sleep outcome. The control apparatus 814 may be a remote server, a remote analysis module, or may be located on the "Cloud".

Figure 9:
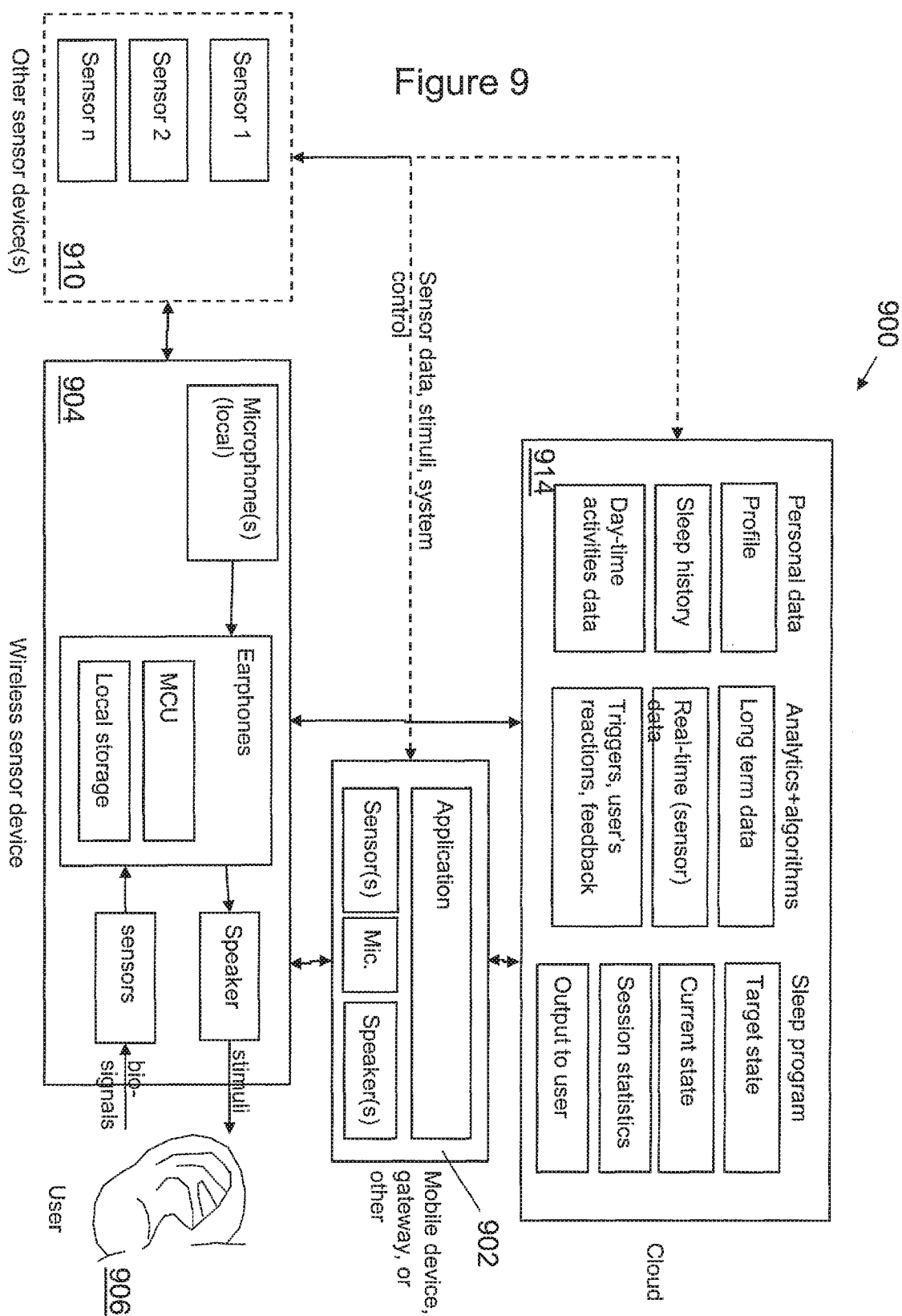
FIG. 9 shows an example system according to the present disclosure.

FIG. 9 shows an example system according to the present disclosure similar to that shown in FIG. 8. FIG. 9 shows an example system 900 according to the present disclosure for a single user 906, but it will be appreciated that, similarly to FIG. 8, there may be a plurality of users 906 each with associated audio output devices 904 and user peripheral/intermediary devices 902.

The system comprises at least a control apparatus 914, and one or a pair of earphones 904 in communication with the control apparatus 914. The control apparatus 914 may be a remote server, a remote analysis module, or may be located on the "Cloud". In some examples, the control apparatus may be located at a user device 902 rather than at the remote server/cloud 914. For example, if the plurality of users is a family sleeping in the same household, the mother's smartphone may comprise (or be) the apparatus and may determine and communicate respective sleeping adjustments comprising audio stimuli to the audio output devices of the members of the household e.g. using the household's Wi-Fi network.

The control apparatus 914 is configured to receive respective sleep profiles of a plurality of users 906, each sleep profile comprising recorded sleep phases of a sleep session of a respective user of the plurality of users 906; receive a target sleep outcome for the plurality of users 906, and based on the respective sleep profiles and the target sleep outcome, determine one or more respective sleep adjustments for provision to at least one of the respective plurality of users 906. The respective sleep adjustments comprise audio stimuli configured to attempt to adjust a respective user's sleep during the respective user's sleep session, or during a subsequent sleep session, in an attempt to achieve, at least in part, the target sleep outcome of the plurality of users 906. The control apparatus 914 is also configured to provide the determined respective sleep adjustments to the plurality of audio output devices 904. The plurality of audio output devices 904 are each configured to receive the determined one or more respective sleep adjustment comprising the audio stimuli from the control apparatus 914 for the user of the plurality of users 906 associated with the audio output device 904, and provide the audio stimuli to the associated user 906 during one or more of the respective user's sleep session and the subsequent sleep session.

The audio output devices 904 in this example may each be comprised in a wireless sensor device 904 comprising earphones/earphones as the audio output apparatus, which themselves comprise a microcontroller unit (MCU) and a local storage unit/memory. The audio output devices 904 in this example also each comprise a local microphone which is configured to detect sounds from the user and/or the ambient surroundings, a speaker configured to provide sounds (audio stimuli) to the user, and one or more sensors/biosensors to detect biosignals from the user, for example to determine the user's sleep habits/phases. The sleep biosignal may comprise one or more of: a position of the user's head; a position of the user's body; motion of the user's head; motion of the user's body; motion of the user's eyes; the heart rate of the user; R-R intervals of the user's heartbeat; the breathing rate of the user; rapid eye movement detection (e.g. using a camera); and the temperature of the user during the sleep session.

A further sensor device 910 may be in communication with the wireless sensor device 904, and be configured to provide one or more other sleep related functions, such as determining a biosignal from the user indicative of sleep. The device 910 may be worn by the user (e.g. a smartwatch, body strap such as a chest strap, or embedded into a garment to be worn by the user), may be proximal to the sleeping user (e.g. in, on, or under a pillow, a mattress, blanket, or headboard/bedframe), or may be remote from the user (e.g. a motion detector, IR camera, or ambient thermometer). Another possible function of the device 910 is to provide one or more stimuli to the user during sleep to help achieve the user's target sleep outcome (e.g. ambient lighting to induce a particular sleep phase). A wearable device 910 may also be used to detect one or more biosignals during the time the user is awake, for example by measuring when the user is walking or running (e.g. a pedometer) or undergoing physical activity (e.g. by measuring changes in sweat produced and heart rate). Such daytime/awake time biosignals may form part of the user's sleep profile, for example, the sleep profile may indicate that the user generally falls into a deeper sleep more quickly if they have done cardio/physical exercise earlier that day.

The control apparatus 914 may determine each user's sleep phases during a sleep session from data recorded by one or more sensors e.g. with the audio output device 904, and/or may determine and/or provide audio stimuli (and any other additional stimuli) to provide to the plurality of users by the earphones 904 during a sleep session to help achieve the target sleep outcome. The control apparatus 914 in this example comprises a personal data file for each of the users, with each user's profile (e.g. name, age, sex, weight, height, ethnicity, profession, known medical issues, other demographics) sleep history (e.g. recorded from one or more previous sleep sessions), and data on each user's daytime activities (e.g. time/duration spend sitting/resting, playing sports, walking, commuting, working etc).

The control apparatus 914 in this example also comprises analytics and algorithms for recording and analysing user data, such as long-term data of each user of the plurality (e.g. any changes in sleep habits detected since using the system 900), real-time sensor data (e.g. detected using the biosignal sensors 904 and/or from other remote sensors 910), and triggers, user reactions and feedback (e.g. current user reactions to provided audio stimuli, and detected biosignals associated with particular detected sleep habits, such as waking following a change in posture or snoring following a user moving into a deeper phase of sleep).

The control apparatus 914 in this example also comprises a sleep program which uses the target state/target sleep outcome, and the current sleep state of each user of the plurality, as well as session statistics (e.g. biosignals detected during the current sleep session) to determine an output to provide to the plurality of users to attempt to achieve the target sleep outcome. For example, the users of the plurality may provide a target of wishing to sleep until 10 am (for example, they may have a late-night meeting the same day, and so wish to wake up later than usual after a longer than usual sleep). The current state may be that one particular user is in REM sleep at 6 am. The session statistics may indicate that the user has had insufficient deep sleep in the current sleep session to feel that they have had enough sleep upon waking for 10 am. The output provided to the user may then be determined to be the provision of audio stimuli (e.g. sounds from nature) to induce a deeper sleep in the user to ensure they do not wake from their current REM state but instead move into Stage 1 (or deeper) sleep, such that when they wake up, closer to 10 am, they have slept for longer and feel refreshed for the evening's meeting. Different audio stimuli may be determined and provided to other user's in the plurality depending on their individual sleep profiles.

For convenience, many of the present examples refer primarily to the provision of the audio stimuli. However, it is to be appreciated, that one or more of the temperature stimuli, vibratory stimuli, and pressure stimuli may be provided additionally or alternatively to the audio stimuli.

In some examples, the apparatus may be configured to determine whether the target sleep outcome has been achieved (and to what extent). For example, if the target sleep outcome is for a plurality of users to feel more refreshed, then one or more biosignals indicative of each user's wellbeing (e.g. heart rate, sweat production, blood pressure) may be monitored to check if the users are in a refreshed state following the sleep session. As another example, if the user is part of a study group and a target sleep outcome is to improve the users' memories, and the apparatus attempted to achieve this goal by attempting to prolong the length of time spent in Stage 2 sleep, for example, then each user's sleep phases may be monitored using one or more biosensors to check if they really did achieve a longer time in Stage 2 sleep. The users may, in some examples, be presented with a cognitive test, for example a memory test, on their smartphone or tablet computer following the sleep session, to check if the users' memories have improved from test results recorded from before the users underwent the sleep sessions in which stimuli were provided.

If a user's biosignals and/or test results indicate that significant progress has been achieved, then the user may continue to be provided with stimuli during sleep to progress further if appropriate (and the user's sleep profile may be updated to reflect the latest results). If a user's biosignals and/or test results indicate that progress has not been achieved sufficiently (e.g. less than a 20% increase in correct test answers, less than a 5% decrease in blood pressure at a particular time of day compared with the measurement taken before the sleep session(s)), then the user may, for example, be provided with different stimuli during sleep to attempt to make progress in achieving the target sleep outcome (and the user's sleep profile may be updated to reflect the latest results). In some examples, continuation of use of the apparatus for a particular target sleep outcome may depend on the user passing one or more post-sleep "tests" (e.g. quiz/test results, and/or particular biosignals being within a predefined range or improved by a predetermined factor).

In some examples, information on external factors may be received by the apparatus during a user's sleep session and taken as input to adjust the target sleep outcome and/or stimuli provided to the user during that sleep session. For example, if the weather forecast indicates that it is likely to rain in the morning after 9 am, a group of users scheduled to meet at work the following morning may receive stimuli to ensure they are awake at 8 am to e.g. travel to work avoiding the rain in time for the group meeting. The accuracy of predicted weather conditions at a particular time may increase closer to the particular time, so the morning weather may be more accurately predicted closer to the morning (during the time the user is asleep) than in the previous evening or earlier.

As another example, real-time (or near-real-time) traffic updates (such as indications of congested or blocked roads, or cancelled trains/flights) may be received prior to or during a user's sleep session and accounted for in determining the stimuli to be provided to the user. For example, if the user's target sleep outcome is to attend a meeting in the next town at 12 noon with colleagues, and during the night a train line which a user would be planning to use (e.g. as determined from the user's calendar/emails) or which the user would be likely to use (e.g. determined from a train line map) is closed, the user may be provided with stimuli to cause them to, for example, wake up earlier than planned to catch an alternative train or consider driving instead so they can meet with their colleagues in time for the meeting.

In some examples, the apparatus may be configured to determine if, in examples where a user of the plurality of users is wearing a wearable device such as an earphone, pair of earphones, or other wearable biosensor, if the item is correctly positioned with respect to the user. If, for example, the user's earphone(s) fall out of the user's ears, then the provision of audio stimuli via the displaced earphone(s) may be e.g. stopped, changed (for example, stereo sound from two earphones may be changed to mono sound provided by one earphone remaining in the user's ear while the displayed earphone is not used), or a power-save mode may be entered.

In some examples, the apparatus may be configured to determine whether the duration of provision of the sleep adjustment for a particular user of the plurality exceeds a predetermined sleep adjustment threshold, and if it does, prevent the provision of further sleep adjustment/audio stimuli to that particular user until the expiry of a sleep adjustment cooling off period. The predetermined sleep adjustment threshold may be a predetermined number of consecutive sleep sessions. For example, to prevent a user becoming dependent on using the apparatus such that healthy sleep without use of the apparatus is not possible, the apparatus may determine that, for example, following seven consecutive nights use to be provided with stimuli, the user may not use the device again for a 72-hour period. Or, if the user wishes to achieve a target sleep outcome for a particular date (e.g. the date of an important meeting) the sleep training/provision of stimuli will not begin earlier than three sleep sessions prior to the meeting and may not be used again following the meeting for 48 hours.

Figure 10:
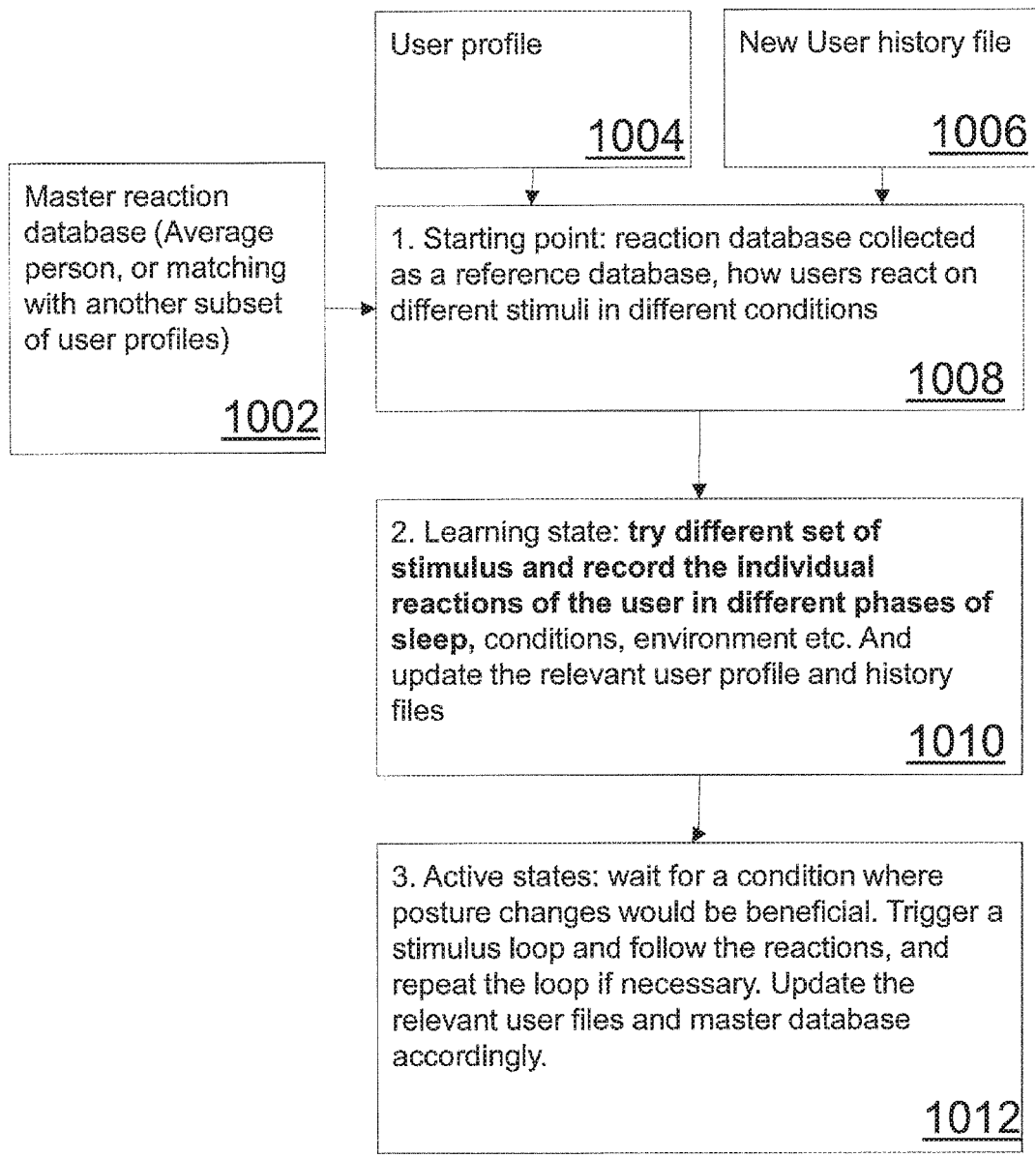
FIG. 10 shows an example method for determining sleep adjustments for a user according to the present disclosure.

FIG. 10 shows an example method for determining sleep adjustments for a user of a plurality of users according to the present disclosure. This method may be carried out for each user of the plurality of users, for example. Initially, the user profile 1004, and the history of the new user 1006 are taken as input. Also, at the start, a master reaction database 1002 is used, which is a database of behaviour and reactions in relation to sleep of the "average person", for example a person of a similar demographic group to the new user. The similar demographic group may be, or may comprise, the other users of the plurality of users.

As a starting point/first step 1008, a reaction database collected as a reference database, which indicates/logs how a user reacts to different stimuli in different conditions. Next is a learning stage 1010, during which different sets of stimuli are tried on the user, and the individual reactions of the user are recorded, in different phases of sleep, conditions, environment etc. The user profile and history files are then updated with this experiment/test information. Finally, in an active state 1012, the method comprises waiting for a condition of the user (e.g. a sleep disorder such as snoring, or a detected unfavourable posture for sleeping) where posture changes would be beneficial. A stimulus loop is then triggered, and the reaction of the user can be followed. This process may be repeated if necessary. The relevant user files and master database are then updated accordingly following provision of the stimuli. In this way the user profile may be tuned to the particular behaviour and requirements of the user to better provide effective audio stimuli to induce sleep adjustments for the user.

While the above discussion uses examples relating to a night's sleep, the examples may also apply equally well for a daytime sleep session (for example, for a group of users who work night shifts), to users who are changing time zones (for example, business travellers flying between time zones), and to users for whom the "sleep session" may not be the predominant sleep session for a 24 hour period, but may be a "power nap" session of a short period of sleep time. In some examples, the apparatus may be configured so that a resting period of a user may be considered to comprise more than one sleep session. For example, if a user wakes up twice during a single night's sleep, then it may be determined that the period of rest comprises three distinct sleep sessions.

In some examples, a sleep adjustment may be configured to attempt to adjust a respective user's sleep during a subsequent sleep session (e.g. following a period of sleep monitoring, or following user provision of a target sleep outcome earlier that day). The "subsequent" nature may be, therefore, following one or more previous sleep sessions, and/or following input prior to the sleep session in which the stimuli are to be provided to the user.

In some examples, a respective sleep adjustment may be configured to attempt to adjust a respective user's sleep at a subsequent time during a current sleep session. That is, the apparatus may be configured to dynamically adjust one or more respective users' sleep "on the fly", during the "current" sleep session, based on sleep profiles (and optionally biosignals) recorded for the plurality of users during a current sleep session. As an example, if a user moves into a sleeping position which is an uncomfortable sleep position (e.g. with the neck bent), this may be detected by e.g. a head-worn gyroscope sensor, and the apparatus may determine and provide stimuli in response to the detection of movement/posture, to induce the user to change to a more comfortable sleeping posture (e.g. neck straight).

An example of providing sleep adjustments on the fly is of a couple with a new puppy. The puppy may need attention during the night when the couple are asleep. To help prevent one partner in the couple always waking up to attend to the puppy, the apparatus may receive a target sleep profile that each partner should have roughly the same amount of similar quality sleep during the night. "On the fly" monitoring of both partners' sleep can allow the apparatus to, for example, determine which partner was the last one to wake up in the night, so that if the puppy yaps for attention later that night, the other partner can be woken up to attend to the puppy. The partner determined to benefit from sleeping through the puppy's yapping may be provided with stimuli to induce sleep, while the partner who needs to be woken up can be provided with stimuli to wake them up to attend to the puppy. Thus, the apparatus may help a group of users to collectively attend to events requiring attention during a sleep session of the users, so that all users are similarly disturbed from sleep (and similarly induced to remain asleep), and all feel similarly refreshed in the morning while the night-time events are still attended to. Of course, if one partner usually has 6 hours sleep a night while the other partner usually has 9, for example, these habits may be accounted for in determine who to wake up and who to keep asleep.

FIG. 11 shows an example method according to the present disclosure. The computer-implemented method comprises: receiving respective sleep profiles of a plurality of users, each sleep profile comprising recorded sleep phases of a sleep session of a respective user of the plurality of users 1100; receiving a target sleep outcome of the plurality of users 1102; and based on the respective sleep profiles and the target sleep outcome, determining one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users 1104.

FIG. 12 shows an example computer-readable medium comprising a computer program configured to perform, control or enable the method of FIG. 10, 11 or any method described herein. The computer program may comprise computer code configured to perform the method(s), such as the method of, receiving respective sleep profiles of a plurality of users, each sleep profile comprising recorded sleep phases of a sleep session of a respective user of the plurality of users 1100; receiving a target sleep outcome of the plurality of users 1102; and based on the respective sleep profiles and the target sleep outcome, determining one or more respective sleep adjustments for provision to at least one of the respective plurality of users, the respective sleep adjustments comprising stimuli configured to attempt to adjust a respective user's sleep during one or more of the respective user's sleep session and a subsequent sleep session, in an attempt to achieve, at least in part, the target sleep outcome of the plurality of users 1104.

In this example, the computer/processor readable medium 1200 is a disc such as a digital versatile disc (DVD) or a compact disc (CD). In other examples, the computer/processor readable medium 1200 may be any medium that has been programmed in such a way as to carry out an inventive function. The computer/processor readable medium 1200 may be a removable memory device such as a memory stick or memory card (SD, mini SD, micro SD or nano SD card).

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some examples, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such examples can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/ circuitry/elements/processor may have other functions in addition to the mentioned functions, and that these functions may be performed by the same apparatus/circuitry/elements/ processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/ position of a circuit board or even the same device. In some examples one or more of any mentioned processors may be distributed over a plurality of devices. The same or different processor/processing elements may perform one or more functions described herein.

It will be appreciated that the term "signaling" may refer to one or more signals transmitted as a series of transmitted and/or received signals. The series of signals may comprise one, two, three, four or even more individual signal components or distinct signals to make up said signaling. Some or all of these individual signals may be transmitted/received simultaneously, in sequence, and/or such that they temporally overlap one another.

With reference to any discussion of any mentioned computer and/or processor and memory (e.g. including ROM, CD-ROM etc.), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed examples may consist of any such individual feature or combination of features. In view of the foregoing description it will be evident to a person skilled in the art that various modifications may be made within the scope of the disclosure.

While there have been shown and described and pointed out fundamental novel features as applied to different examples thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/ or described in connection with any disclosed form or example may be incorporated in any other disclosed or described or suggested form or example as a general matter of design choice. Furthermore, in the claims means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
   at least one processor; and
   at least one memory including computer program code, the at least one memory and the computer program code configured to, with the at least one processor, cause the apparatus to perform at least the following:
   receive sleep profiles of a plurality of users forming a group having a target sleep outcome based on a non-sleep-related event, the sleep profiles being collected for the formed group, at least some of the sleep profiles comprising respective recorded sleep phases of a sleep session of a respective user of the plurality of users;
   receive the target sleep outcome of the plurality of users, the target sleep outcome being based on individual sleep habits of the plurality of users; and
   based on the respective sleep profiles and the target sleep outcome of the plurality of users, determine two or more respective sleep adjustments for provision to at least two of the respective plurality of users, the respective sleep adjustments comprising stimuli configured to attempt to adjust a respective user's sleep during one or more of the respective user's sleep session or a subsequent sleep session, in an attempt to achieve, at least in part, the target sleep outcome of the plurality of users;
   wherein the target sleep outcome of the plurality of users is associated with different individual respective sleep adjustments for provision to at least two or more of the plurality of users.

2. The apparatus of claim 1, wherein the plurality of users is an established user group, the established user group having a predetermined common goal related to the non-sleep-related event.

3. The apparatus of claim 2, wherein the target sleep outcome of the plurality of users is set for each of the plurality of users such that the plurality of users achieves the common goal.

4. The apparatus of claim 1, wherein the memory and computer program code are configured to, with the processor, cause the apparatus to determine the respective one or more sleep adjustments of the one or more of the plurality of users by using respective sleep biosignals recorded during a sleep session of the plurality of users.

5. The apparatus of claim 4, wherein the sleep biosignal comprises one or more of: a position of a user's head; a position of a user's body; motion of a user's head; motion of a user's body; a heart rate of a user; a breathing rate of a user; or a temperature of a user during the sleep session, the user being of the plurality of users.

6. The apparatus of claim 1, wherein the target sleep outcome of the plurality of users comprises one or more of: two or more of the plurality of users awaking at the same time; one or more of the plurality of users awaking within a predetermined time window; two or more of the plurality of users awaking following being asleep for the same amount of time; or two or more of the plurality of users having an asleep-awake daily routine in the same time zone.

7. The apparatus of claim 1, wherein the target sleep outcome of the plurality of users is one or more of: determined by the apparatus based on the received respective sleep profiles; input by one of the plurality of users; or input by a secondary user other than any of the plurality of users.

8. The apparatus of claim 1, wherein the memory and computer program code are configured to, with the processor, cause the apparatus to: receive respective awake profile data for two or more of the plurality of users, the respective awake profile data comprising a record of activities during a period of being awake for one or more of the respective users; and determine the two or more respective sleep adjustments further based on the awake profile data for the two or more of the respective users.

9. The apparatus of claim 1, wherein the respective one or more sleep adjustments comprises stimuli configured to attempt to adjust the sleep of a user of the plurality of users during one or more of the sleep session or the subsequent sleep session by inducing an adjustment in sleeping posture of the user.

10. The apparatus of claim 1, wherein the stimuli are configured to be provided to a user of the plurality of users by one or a pair of earphones to be worn by the user during one or more of the sleep session or the subsequent sleep session.

11. The apparatus of claim 1, wherein the apparatus is a server remote from and in communication with a plurality of output devices, the plurality of output devices configured to provide the stimuli to the plurality of users.

12. The apparatus of claim 1, wherein the memory and computer program code are configured to, with the processor, cause the apparatus to determine one or more awake instructions for provision to one or more users of the plurality of users, the awake instructions indicating an activity for a user of the plurality of users to perform to support the attempt to adjust that user's sleep during one or more of the sleep session or the subsequent sleep session in the attempt to achieve, at least in part, the target sleep outcome of the plurality of users.

13. The apparatus of claim 1, wherein the sleep adjustment comprises one or more of: audio stimuli, vibratory stimuli, temperature stimuli, and pressure stimuli.

14. The apparatus of claim 13, wherein audio stimuli comprise audio information for provision to one or more users of the plurality of users during one or more sleep phases most conducive to a respective user retaining the audio information.

15. The apparatus of claim 1, wherein when a subsequent sleep session is to be attempted to be adjusted according to the target sleep outcome of the plurality of users, the sleep profiles of a plurality of users comprise recorded sleep phases of a previous sleep session of a respective user of the plurality of users.

16. The apparatus of claim 1, wherein the memory and computer program code are configured to, with the processor, cause the apparatus to determine whether the duration of provision of the sleep adjustment exceeds a predetermined sleep adjustment threshold, and if it does, prevent the provision of further sleep adjustment until the expiry of a defined period of time.

17. The apparatus of claim 1, wherein the memory and computer program code are configured to, with the processor, cause the apparatus to determine respective series of incremental sleep adjustments for provision to the plurality of users over a plurality of sleep sessions to achieve the target sleep outcome of the plurality of users.

18. A system comprising: a control apparatus; and a plurality of output devices in communication with the control apparatus; the control apparatus configured to:

receive respective sleep profiles of a plurality of users forming a group having a target sleep outcome based on a non-sleep-related event, the sleep profiles being collected for the formed group, at least some of the sleep profiles comprising respective recorded sleep phases of a sleep session of a respective user of the plurality of users;

receive the target sleep outcome of the plurality of users, the target sleep outcome being based on individual sleep habits of each of the plurality of users; and based on the respective sleep profiles and the target sleep outcome of the plurality of users, determine two or more respective sleep adjustments for provision to at least two of the respective plurality of users, the respective sleep adjustments comprising stimuli configured to attempt to adjust a respective user's sleep during one or more of the respective user's sleep session or a subsequent sleep session in an attempt to achieve, at least in part, the target sleep outcome of the plurality of users; and provide the determined two or more respective sleep adjustments to the plurality of output devices; the plurality of output devices configured to: receive the determined two or more respective sleep adjustments comprising the stimuli from the control apparatus for the user of the plurality of users associated with that output device, and provide the stimuli to the associated user during one or more of the respective user's sleep session or the subsequent sleep session;

wherein the target sleep outcome is associated with different individual respective sleep adjustments for provision to at least two or more of the plurality of users.

19. A computer-implemented method comprising:

receiving respective sleep profiles of a plurality of users forming a group having a target sleep outcome based on a non-sleep-related event, the sleep profiles being collected for the formed group, at least some of the sleep profiles comprising respective recorded sleep phases of a sleep session of a respective user of the plurality of users;

receiving the target sleep outcome of the plurality of users, the target sleep outcome being based on individual sleep habits of each of the plurality of users; and based on the respective sleep profiles and the target sleep outcome of the plurality of users, determining two or more respective sleep adjustments for provision to at least two of the respective plurality of users, the respective sleep adjustments comprising stimuli configured to attempt to adjust a respective user's sleep during one or more of the respective user's sleep session or a subsequent sleep session, in an attempt to achieve, at least in part, the target sleep outcome of the plurality of users;

wherein the target sleep outcome is associated with different individual respective sleep adjustments for provision to at least two or more of the plurality of users.

20. A non-transitory computer readable medium comprising program instructions stored thereon, for performing at least the following:

receiving respective sleep profiles of a plurality of users forming a group having a target sleep outcome based on a non-sleep-related event, the sleep profiles being collected for the formed group, at least some of the sleep profiles comprising respective recorded sleep phases of a sleep session of a respective user of the plurality of users;

receiving the target sleep outcome of the plurality of users, the target sleep outcome being based on individual sleep habits of each of the plurality of users; and based on the respective sleep profiles and the target sleep outcome, determining two or more respective sleep adjustments for provision to at least two of the respective plurality of users, the respective sleep adjustments comprising stimuli configured to attempt to adjust a respective user's sleep during one or more of the respective user's sleep session or a subsequent sleep session, in an attempt to achieve, at least in part, the target sleep outcome of the plurality of users;

wherein the target sleep outcome is associated with different individual respective sleep adjustments for provision to at least two or more of the plurality of users.

\* \* \* \* \*